United States Patent
Rubenstein

[19]

[11] Patent Number: 5,879,881
[45] Date of Patent: Mar. 9, 1999

[54] SOLID PHASE SYSTEM FOR USE IN LIGAND-RECEPTOR ASSAYS

[75] Inventor: Albert S. Rubenstein, Bierges, Belgium

[73] Assignee: Hybritech, Incorporated, San Diego, Calif.

[21] Appl. No.: 162,791

[22] Filed: Dec. 7, 1993

Related U.S. Application Data

[63] Continuation of Ser. No. 879,693, May 5, 1992, abandoned, which is a continuation of Ser. No. 579,087, Sep. 7, 1990, abandoned, which is a continuation of Ser. No. 3,496, Jan. 15, 1987, abandoned, which is a continuation-in-part of Ser. No. 847,799, Apr. 3, 1986, abandoned, which is a continuation-in-part of Ser. No. 720,036, Apr. 4, 1985, abandoned.

[51] Int. Cl.$^6$ ....................... G01N 33/546; G01N 33/569
[52] U.S. Cl. ................................... 435/5; 422/55; 422/56; 422/58; 422/61; 435/6; 435/7.1; 435/7.2; 435/7.33; 435/7.36; 435/7.9; 435/7.92; 435/7.93; 435/7.94; 435/7.95; 435/287.1; 435/287.2; 435/287.7; 435/287.8; 435/805; 435/810; 436/515; 436/518; 436/523; 436/531; 436/533; 436/534; 436/540; 436/810
[58] Field of Search .................................. 422/55–58, 61; 435/6, 7.1, 7.2, 7.33, 7.36, 7.9, 5, 7.92–7.95, 967, 970, 973, 287.1, 287.2, 287.7, 287.8, 287.9, 805, 810; 436/501, 515, 518, 523, 531, 540, 548, 807, 810, 824, 533, 534

[56] References Cited

U.S. PATENT DOCUMENTS

| | | | |
|---|---|---|---|
| 3,964,467 | 6/1976 | Rose | 424/101 |
| 4,166,102 | 8/1979 | Johnson | 424/1 |
| 4,280,816 | 7/1981 | Elahi | 23/230 B |
| 4,294,817 | 10/1981 | Burgett et al. | 424/8 |
| 4,338,094 | 7/1982 | Elahi | 435/7 |
| 4,340,564 | 7/1982 | Harte et al. | 422/56 |
| 4,366,241 | 12/1982 | Tom et al. | 435/7 |
| 4,378,344 | 3/1983 | Zahradnik et al. | 436/500 |
| 4,381,921 | 5/1983 | Pierce et al. | 436/535 |
| 4,399,229 | 8/1983 | Kelton et al. | 436/519 |
| 4,424,279 | 1/1984 | Bohn et al. | 436/534 |
| 4,446,232 | 5/1984 | Liotta | 435/7 |
| 4,472,498 | 9/1984 | Masuda et al. | 435/7 |

(List continued on next page.)

FOREIGN PATENT DOCUMENTS

| | | |
|---|---|---|
| 0 066 648 | 12/1982 | European Pat. Off. . |
| 69869 | 1/1983 | European Pat. Off. . |
| 0 119 622 | 9/1984 | European Pat. Off. . |
| 0119623 | 9/1984 | European Pat. Off. ............ 422/56 |
| 119 623 | 9/1984 | European Pat. Off. . |
| 191640 | 2/1986 | European Pat. Off. . |
| 217403 | 4/1987 | European Pat. Off. . |
| 57-200862 | 12/1982 | Japan . |
| 58-9070 | 1/1983 | Japan . |
| 58-76763 | 5/1983 | Japan . |
| 59-102388 | 6/1984 | Japan . |
| 59-170768 | 9/1984 | Japan . |
| 2 099 578 | 12/1982 | United Kingdom . |
| 2 111 676 | 7/1983 | United Kingdom . |
| 8402004 | 5/1984 | WIPO . |
| 8403151 | 8/1984 | WIPO . |

OTHER PUBLICATIONS

Harold H. Handley et al., "Development of a Rapid MicroELISA Assay for Screening Hybridoma Supernatants for Murine Monoclonal Antibodies," Journal of Immunological Methods, 54 (1982) pp. 291–296.

Edberg, S., *Yale Journal of Biology & Medicine*, 58: 425 (1985).

*Primary Examiner*—Christopher L. Chin
*Attorney, Agent, or Firm*—William H. May; Margaret A. Kivinski; Finnegan, Henderson, Farabow, Garrett & Dunner

[57] ABSTRACT

A solid phase system for use in ligand-receptor assays, particularly immunoassays using monoclonal antibodies, is disclosed. The solid phase system comprises a porous matrix in which microspheres, bound with a receptor capable of capturing a target ligand, are entrapped. Preferably, the microspheres are entrapped within a discrete zone or zones of the porous matrix.

125 Claims, 1 Drawing Sheet

U.S. PATENT DOCUMENTS

| | | | |
|---|---|---|---|
| 4,514,508 | 4/1985 | Hirschfeld | 436/821 |
| 4,540,659 | 9/1985 | Litman et al. | 435/7 |
| 4,552,839 | 11/1985 | Gould et al. | 435/7 |
| 4,563,417 | 1/1986 | Albarella et al. | 435/6 |
| 4,587,102 | 5/1986 | Nagamoto et al. | 422/56 |
| 4,632,901 | 12/1986 | Valkirs et al. | 435/5 |
| 4,657,739 | 4/1987 | Yasuda et al. | 422/56 |
| 4,727,019 | 2/1988 | Valkirs et al. | 435/5 |
| 4,740,468 | 4/1988 | Weng et al. | 435/7 |
| 4,861,552 | 8/1989 | Masuda et al. | |
| 5,026,653 | 6/1991 | Lee et al. | 436/518 |
| 5,236,826 | 8/1993 | Marshall | |
| 5,501,949 | 3/1996 | Marshall | |

SOLID PHASE SYSTEM FOR USE IN LIGAND-RECEPTOR ASSAYS

CROSS REFERENCE TO RELATED APPLICATIONS

This application is a continuation of application Ser. No. 07/879,693, filed May 5, 1992, now abandoned, which is a continuation of application Ser. No. 07/579,087, filed Sep. 7, 1990, now abandoned, which is a continuation of application Ser. No. 07/003,496, filed Jan. 15, 1987, now abandoned, which is a continuation-in-part of application Ser. No. 06/847,799, filed Apr. 3, 1986, now abandoned, which is a continuation-in-part of application Ser. No. 06/720,036, filed Apr. 4, 1985, now abandoned.

This application is a continuation-in-part of A. Rubenstein, Ser. No. 847,799, filed Apr. 3, 1986, which is a continuation-in-part of A. Rubenstein, Ser. No. 720,036, filed Apr. 4, 1985. This application relates to the subject matter of G. Valkirs et al., Ser. Nos. 609,395 and 733,292, filed May 11 1984 and May 10, 1985, respectively, now U.S. Pat. Nos. 4,632,901 and 4,727,019, respectively and G. Valkirs et al., Ser. No. 924,006, filed Oct. 28, 1986. This application also relates to the subject matter of G. Valkirs et al., Ser. No. 842,611, filed Mar. 21, 1986. The disclosures of all these references are incorporated by reference herein.

FIELD OF INVENTION

This invention relates to ligand-receptor assay processes. In another aspect, it relates to a solid phase system for use in ligand-receptor assays, particularly immunoassays using monoclonal antibodies.

BACKGROUND

Ligand-receptor assays, particularly immunoassays, provide sensitive diagnostic tools for the in vitro detection in serum and other body fluids of analytes associated with disease and other physiological conditions of clinical significance.

In the past, immunoassays have typically relied on a polyclonal antibody preparation bound to a solid phase. In such assays, a solution of antigen labeled to permit detection is allowed to compete with antigen in a sample for the solid phase antibody. The extent to which the labeled antigen is bound to the solid phase or is detected in the liquid phase can be used as a measure of the presence and quantity of antigen in the sample being analyzed.

Subsequently, non-competitive immunometric assays became available. In these assays, a polyclonal antibody preparation bound to a solid phase is also used. The sample containing the suspected antigen is allowed to contact the solid phase in order for the antigen to bind to the antibodies on the solid phase. Typically, after an incubation step the sample is separated from the solid phase which is then washed and incubated with a solution of additional polyclonal antibodies which has been labeled, for example with a radionuclide, an enzyme, or a fluorescent moiety, to permit detection.

After this second incubation, the unbound labeled antibody is separated from the solid phase and the amount of labeled antibody in either the liquid phase or bound to the solid phase in an antibody:antigen:antibody sandwich is determined as a measure of the presence and/or concentration of antigen in the sample tested.

More recently, immunoassay processes have been modified to use monoclonal antibodies. For example, U.S. Pat. No. 4,376,110 describes two-site immunometric assays using pairs of monoclonal antibodies, one bound to a solid phase and the other labeled to permit detection. The use of monoclonal antibody pairs which recognize different epitopic sites on an antigen has made it possible to conduct simultaneous immunometric assays in which the antigen and labeled antibody incubations do not require the intermediate steps of prior processes.

In the foregoing immunoassay processes, the solid phase system typically comprises an antibody bound to a bead, or alternatively, an antibody coated on a material such as a membrane or filter, suitable to capture an antigen of interest. At present, the preparation of such solid phase systems characteristically requires activation procedures to facilitate the coating of an antibody to a solid support. Additionally, a backcoating procedure, involving the coating of the solid support with a substance effective to inhibit non-specific binding, is generally required. The activation and backcoating procedures are time-consuming and difficult procedures, and as a result, render the preparation of solid phase systems very costly.

In addition to the above-described limitations associated with the preparation of solid phase systems presently available, it has not been possible to assay a given sample for more than one analyte of interest simultaneously on a single solid phase system. Further, present solid phase systems lack the internal controls (i.e., positive and negative controls) which are essential for a determination of the validity and reliability of an assay. The preparation of solid phase systems for a multiple immunoassay process and/or an internal control system has been, prior to the present invention, very difficult.

Accordingly, there exists a need for a solid phase system which may be prepared more efficiently and which minimizes the difficulty and expense of preparation. Additionally, there exists a need for an improved solid phase system which may be utilized to assay a sample for at least two analytes of interest simultaneously. Further, there exists a need for an improved solid phase system which permits the incorporation of internal controls for the performance of assays.

SUMMARY OF THE INVENTION

The present invention provides a solid phase system for use in ligand-receptor assays, particularly immunoassays, for the detection of a selected analyte in a fluid sample. As used herein, the term "ligand-receptor assay" refers to an assay for an analyte which is detected by the formation of a complex between a ligand and another substance capable of specific interaction with the ligand, i.e., receptor. The ligand may be the analyte itself or a substance which if detected can be used to infer the presence of the analyte in a sample. Persons skilled in the art will appreciate that, depending upon the analyte of interest, a member of a specific binding pair may be either receptor or ligand depending upon assay design. In the context of the present invention, the term "ligand" encompasses antigens, haptens, antibodies, deoxyribonucleic acid (DNA), ribonucleic acid (RNA), hormones, metabolites and other naturally occurring substances of diagnostic interest having a specific binding partner therefor, i.e., the receptor of the ligand-receptor assay.

The solid phase system of the invention comprises a porous matrix, such as a membrane or filter, within which microspheres are entrapped. Preferably, the microspheres are entrapped within a discrete or defined zone of the matrix.

Additionally, the microspheres, selected to have a size compatible with the pore size of the porous matrix, are bound with a receptor such as an antibody, preferably a monoclonal antibody, antigen, nucleic acid sequence or other substance capable of capturing the selected ligand when exposed to a sample containing the ligand. For example, the microspheres may be bound with an allergen capable of capturing an IgE antibody in a sample which is specific for the bound allergen.

In preferred solid phase systems, distinct groups of microspheres to which are bound an antibody, antigen or other suitable receptor substance are entrapped within discrete zones of the porous matrix so as to permit the performance of a multiple assay for the detection of at least two selected analytes. Further, distinct groups of microspheres may be entrapped within the porous matrix so as to incorporate internal control systems for the detection of selected analytes.

The present invention is also directed to an apparatus comprising, as a first porous member, a solid phase system as described above. The preferred apparatus comprises, as a second member, means associated with the solid phase system to permit the flow of a fluid sample through the solid phase system. Alternative preferred apparatus further comprise a porous member or members which separate the first porous member from the second absorbent member. The terms "solid phase system" and "first porous member" are used interchangeably herein.

The present invention is further directed to a ligand-receptor assay process comprising, as a first step, the introduction of a fluid sample onto the solid phase system whereby, as the fluid flows through the solid phase system, the receptor bound to the microspheres captures the selected target ligand. Following the addition of the sample, a solution of a receptor conjugate capable of binding the target ligand and labeled so as to permit detection is added to the solid phase system. As used herein the term "receptor conjugate" refers to a complex comprising a receptor and a label capable of detection. In the case of an immunometric assay for a target antigen, the receptor conjugate may be a labeled antibody, preferably a monoclonal antibody. Alternatively, if the target ligand is an antibody, labeled antigen may be used as the receptor conjugate. Unbound receptor conjugate may thereafter be removed by a washing step. The presence of bound receptor conjugate on the solid phase system is then determined as an indication of the presence of the analyte in the sample.

This invention has been summarized in order that the drawings and detailed description that follow may be better understood and the contribution to the art may be better appreciated.

DETAILED DESCRIPTION OF THE INVENTION

As indicated above, the present invention provides a solid phase system for use in ligand-receptor assays, particularly immunoassays, for the detection of a selected analyte in a fluid sample. In accordance with the present invention, the solid phase system comprises a porous matrix in which microspheres may be entrapped. A variety of porous matrices, including natural and synthetic matrices, may be suitably utilized provided microspheres of a size compatible with the pore size of the matrix may be entrapped in accordance with the invention. Among the matrices preferred for use are membranes or filters comprised of glass fibers, nylon, or ceramic materials having a defined porosity.

The solid phase system further comprises microspheres to which are bound a selected receptor, such as an antibody, preferably a monoclonal antibody, antigen or other suitable receptor substance capable of capturing the ligand of interest. Microspheres comprised of a polymeric material such as latex, polyethylene, polypropylene or polystyrene are preferred for use in the present invention. However, it will be recognized by those skilled in art that a variety of microspheres, comprised of either natural or synthetic materials, may be utilized. In the case of polymers, the polymer is selected on the basis of its ability to facilitate binding with the selected member of the ligand-receptor pair, e.g., it may be a polymer or copolymer having a functional group which facilitates binding by covalent bond formation or by a coating operation. Additionally, the microspheres are selected to have a size effective to permit their entrapment within the porous matrix as well as the rapid flow of fluid around the microspheres and through the matrix. Preferred for use are microspheres having a size within the range of from about 0.1 to about 50 microns in diameter. We have found that microspheres having a size within this range tend to maximize the effective surface area available for reaction with the target ligand as aggregation and adhesion of the microspheres within the matrix is minimized. Particularly preferred for use are microspheres having a size within the range of from about 0.1 to about 2.0 microns in diameter; microspheres having a size within this range tend to enhance the contact and kinetics for reaction between receptor bound to the microspheres and the target ligand.

In accordance with the present invention, the microspheres selected for use are activated with a suitable receptor, e.g., an antibody, antigen or other biological substance suitable for use as a receptor to bind and capture the target ligand. Activation may be achieved by covalent binding or, in appropriate cases, by application of a coating of the receptor on the microspheres. In the case of an immunoassay to determine the presence of an antigen in a sample, the receptor is preferably a monoclonal antibody, however, polyclonal antibodies from antisera may be suitably used. Techniques for the coating or covalent binding of proteins to microspheres as well as for monoclonal and polyclonal antibody preparation, are well known to the art and require no repetition herein. The activated microspheres are entrapped in the matrix, preferably within a defined zone or zones of the matrix and in a predetermined pattern. Additionally, we have unexpectedly found that it is desirable to use an extremely low concentration of activated microspheres in solution for entrapment, preferably within the range of from about 0.01 to 1.0%, to provide increased sensitivity in an assay. The means for entrapment of the microspheres within the matrix is not critical and a variety of means may be used. For example, the microspheres may be added to the surface of the porous matrix as a suspension in a suitable liquid vehicle, for example, as a polymer latex, preferably a monodisperse latex, which is subsequently removed in a drying step. Gravity, a vacuum or capillary action may be used to draw the microspheres into discrete zones within the porous matrix prior to removal of the vehicle. As the microspheres are activated prior to entrapment, the present invention overcomes limitations associated with the preparation of the solid phase systems of the prior art.

In accordance with the present invention, the receptor-bound microspheres are preferably entrapped within the matrix in a manner which permits their mobility within the matrix and inhibits their agglutination or aggregation within the matrix, and further, which permits rapid fluid flow through the matrix and around the particles. While applicant does not intend to be bound by any theory, it is believed that the free movement of microspheres within the matrix may enhance the contact between receptor bound to the microspheres and the target ligand and permits effective washing during an assay process. Additionally, as indicated above, to attain the desired sensitivity of an assay process, the number and size of the entrapped microspheres must be optimized within the ranges set forth herein. Further, the microspheres may be coated prior to entrapment to minimize or inhibit their aggregation and adhesion within the matrix.

Figure 1:
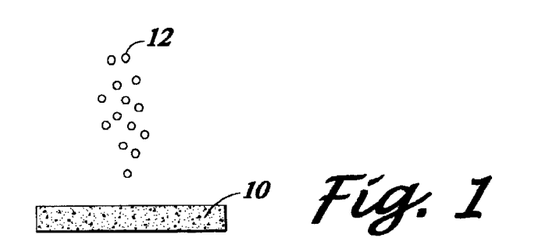
FIG. 1 is a conceptualization of a porous matrix useful in the present invention and the manner of addition of microspheres thereto.
Figure 2:
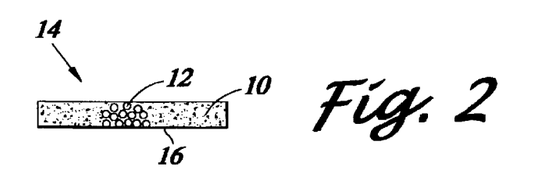
FIG. 2 is a conceptualization of a cross section of a solid phase system of the present invention.
Figure 3:
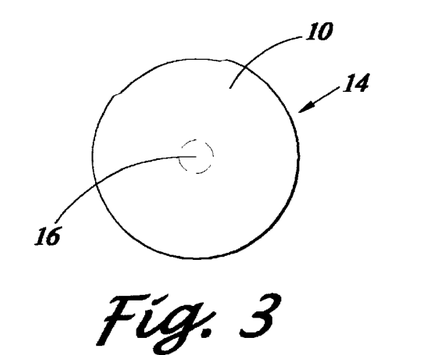
FIG. 3 is a top view of a solid phase system of the present invention for the detection of a single analyte in a sample.

Turning now to FIG. 1, there is shown in cross section a conceptualization of a porous matrix 10 useful in the present invention and the manner of addition of activated microspheres 12 thereto (microsphere vehicle is not shown). In FIG. 2 there is shown in cross section a conceptualization of a solid phase system 14 of the present invention. Thus, in FIG. 2, the porous matrix 10 is shown having the activated microspheres 12 entrapped in a defined or discrete zone 16 within the matrix 10. A top view of the solid phase system 14 for use in an assay for the detection of a single analyte, as conceptualized in FIG. 2, is illustrated in FIG. 3. Accordingly, in FIG. 3, there is shown the discrete zone 16 in which microspheres 12 are entrapped for the capture of a ligand within the matrix 10 of the solid phase system 14.

A preferred solid phase system of the present invention comprises plural groups of microspheres entrapped in discrete zones, preferably in a predetermined pattern, within the matrix. Each group of microspheres is bound, prior to entrapment, with a different receptor, such as an antibody or antigen capable of capturing a different ligand of interest. Accordingly, in one embodiment of the invention, each group of microspheres comprises a population of microspheres bound with the same antibody, antigen or other receptor selected for use in the assay. Alternatively, a group of microspheres may comprise a mixture of microspheres to which are bound different receptors. For example, in the case of an immunoassay for an antigen, each group of microspheres may comprise at least two subpopulations of microspheres wherein each subpopulation is bound with an antibody, preferably a monoclonal antibody, capable of binding with a different determinant or epitope of the antigen. Preferably, the monoclonal antibodies bound with the subpopulations of microspheres comprising a distinct group of microspheres are selected to have a specific reactivity with non-interfering epitopes of the target ligand, thereby enhancing the sensitivity and specificity of the assay.

Accordingly, a solid phase system as described above is useful in a multiple ligand-receptor assay for the simultaneous detection of at least two selected analytes in a given sample. In the case of an immunoassay, the presence of different analytes within a sample may be detected simultaneously by a distinct color reaction for each analyte by the use of different enzyme labeled antibodies which generate distinct color reactions upon addition of a suitable substrate. Alternatively, different groups of microspheres may be entrapped within the porous matrix in a way which permits their identification by reason of their particular location in the matrix.

Further, the preferred solid phase system as described above is particularly useful where it is highly desirable to simultaneously determine the presence of more than one analyte of interest in a sample, such as for the determination of causative agents of an allergic response. This may be readily accomplished by entrapping distinct groups of microspheres, each of which is bound with one of a group of specific allergens (i.e., proteins or carbohydrates which are suspect in eliciting an immune response), within discrete zones of the matrix. Such a solid phase system provides, in essence, a panel of allergens capable of capturing IgE antibodies which may be present in a patient serum sample. Accordingly, the pattern of reactivity on the solid phase system, as determined by the presence of allergen-specific IgE antibodies in a given sample, provides an indication of the allergens eliciting a given allergic response. In such assays, typically the allergen-IgE pairs are detected by using labeled anti-IgE antibody as described in U.S. Pat. No. 3,720,760.

Figure 4:
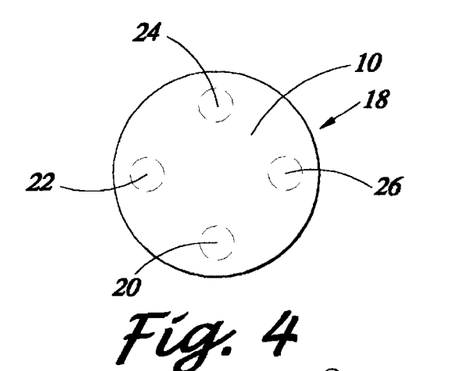
FIG. 4 is a top view of a preferred solid phase system of the present invention for the multiple detection of different analytes in a sample.

Referring now to FIG. 4, there is shown a top view of a preferred solid phase system 18 for use in a multiple assay process in accordance with the conceptualization of a solid phase system 14 in FIG. 2. Thus, in FIG. 4 there is shown a matrix 10 in which there are discrete zones 20, 22, 24 and 26 comprising groups of microspheres, each of which is activated with a different receptor for the capture of different ligands of interest on the solid phase system 18.

Further in accordance with the present invention, a preferred solid phase system comprises distinct groups of microspheres as an internal control system (i.e., positive and/or negative controls). For example, the microspheres comprising a positive control may be bound with the target ligand or other suitable receptor substance capable of mimicing the binding of the target ligand. By comparison, the microspheres comprising a negative control are either without a bound component or, preferably, bound with a substance, e.g. antibody or antigen or DNA as the case may be, which is incapable of capturing the ligand of interest but which is capable of mimicing the non-specific binding interactions of the microsphere-bound receptor with components of the sample other than the target ligand. Such a solid phase system, which may be utiliized in a single or multiple assay, provides a means for determining the validity and reliability of the assay. Thus, in an immunoassay, the incorporation of a negative control provides a means for determining whether a false positive result, generally attributable to the nonspecific binding of a sample component with the receptor, has occurred. A positive control, on the other hand, reduces the likelihood that a false negative result will go undetected.

Additionally, the present invention provides a means for incorporating internal references for qualitative and quantitative determinations of a target ligand in an assay process as set forth and described in the co-pending application of G. Valkirs et al., Ser. No. 842,611, filed Mar. 21, 1986, and incorporated by reference herein.

Figure 5:
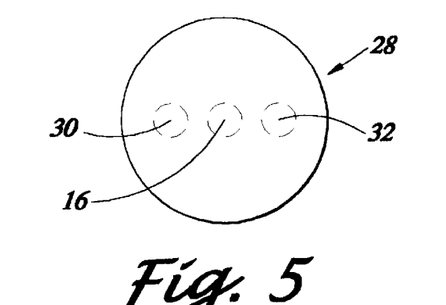
FIG. 5 is a top view of a preferred solid phase system of the present invention for the detection of a single analyte in a sample including internal positive and negative controls.

Turning now to FIG. 5, there is shown a top view of a preferred solid phase system 28 as described above for the detection of a single analyte and which incorporates internal controls. Thus, FIG. 5 depicts, consistent with the conceptualization of FIG. 2, a solid phase system 28 having a discrete zone 16 within the matrix 10 comprising microspheres to which the selected receptor is bound. Discrete zone 30 within the matrix 10 comprises microspheres to which the target ligand is bound as a positive control and discrete zone 32 within matrix 10 comprises microspheres which are preferably coated with a substance which mimics the non-specific binding characteristics of the receptor as a negative control. Thus, when system 28 is used in an assay of a patient sample which contains the analyte of interest, both zone 16 and 30 should indicate a positive result. On the other hand, a change in zone 32 corresponding with a change in zone 16 would be interpreted as a false positive result.

The apparatus of the present invention comprises, as a first porous member, a solid phase system as described above. The apparatus further comprises additional means, operatively associated with the first porous member, for facilitating the flow of a fluid sample and liquid reagents through the first member. For example, a vacuum source or capillary action below the first porous member may be utilized to draw liquid through the first member. Alternatively, means for applying a pressure above the first porous member may be utilized to facilitate the flow of a fluid sample and liquid reagents through the first member.

In a preferred embodiment of the apparatus, a second absorbent member is associated with the solid phase system so as to permit the flow of a fluid sample through the first porous member and into the absorbent material. The second absorbent member, having a surface over which the first member may be placed, has capillaries therethrough in a direction generally transverse to the surface over which the first porous member is placed such that the capillaries are in direct communication with the pores of the first member. A variety of materials may be used for the second absorbent member, such as cellulose acetate fibers or polyester.

In an alternative preferred embodiment, the apparatus further comprises a third porous member which separates the first porous member and the second absorbent member. The third porous member permits the flow of a fluid sample through the first member and into the second absorbent member and, additionally, may function as a support member. The third porous member may be a porous disk, such as a polyethylene disk, and rests upon the second absorbent member such that the absorbent member is in capillary communication with the pores of the first member via the third porous member.

In yet another preferred embodiment, the apparatus further comprises a fourth porous member which separates the first porous member and the third porous member and maintains the flow of a fluid sample through the first porous member and into the second absorbent member. The fourth member may be comprised of a variety of materials, such as glass fibers or polyester.

Specific apparatus incorporating the preferred embodiments may be constructed, for example, essentially as described in the co-pending application of G. Valkirs et al., Ser. No. 924,006, filed Oct. 28, 1986, and the applications of G. Valkirs et al., Ser. Nos. 609,395, and 733,292, filed May 11, 1984 and May 10, 1985, respectively, now U.S. Pat. Nos. 4,632,901 and 4,727,019, respectively. An illustration of such an apparatus is provided by reference to FIG. 6. Accordingly, in FIG. 6, a first porous member comprising a solid phase system 14, such as the solid phase system depicted in top view by FIG. 3 and conceptualized in cross section by FIG. 2, is shown. The first porous member 14 of the apparatus 34 rests on an optional fourth porous member 40 and an optional third porous member 36 which permits and maintains the flow of a fluid sample through the first porous member 14 and into a second absorbent member 38.

As previously indicated, the solid phase system and apparatus of the present invention are of significant utility in the performance of ligand-receptor assays, particularly multiple ligand-receptor assays for the detection of at least two analytes of interest and/or ligand-receptor assays incorporating an internal control system. While the present invention is particularly useful for the performance of immunoassays, those skilled in the art will appreciate that with suitable modification, the solid phase system provided by the invention may be utilized for other ligand-receptor assays, including assays involving nucleic acid probe technology.

In accordance with the ligand-receptor processes of the invention, a fluid sample suspected of containing the analyte (s) of interest is introduced onto the solid phase system of an apparatus as described above. In the case of an immunoassay, the solid phase preferably incorporates as a receptor a monoclonal antibody bound to the microspheres, although a polyclonal antibody preparation may be used when the ligand of interest is an antigen. If the ligand of interest is an antibody, however, the solid phase may comprise an antigen for which the antibody to be detected is specific. Following the flow of fluid sample through the solid phase system and into the absorbent member, a solution of receptor conjugate, capable of binding with the target ligand and labeled so as to permit detection, is added. In the case of immunoassays, the receptor conjugate may be an antibody, preferably a monoclonal antibody, or antigen capable of binding with the ligand of interest. The addition of receptor conjugate, as appropriate, permits the formation of a complex with the ligand captured by the solid phase system. In the case of an immunoassay, if the microspheres comprising the solid phase system are bound with monoclonal antibody, and the labeled antibody is also a monoclonal antibody, the two antibodies are selected to bind to non-interfering binding sites of the antigen, essentially as described in U.S. Pat. No. 4,376,110 and U.S. Pat. No. 4,486,530, the disclosures of which are incorporated by reference. In presently preferred embodiments, the receptor conjugate is labeled with an enzyme, however other conventional labels, such as radionuclides, fluorescent agents, phosphorescent agents and polymers containing dyes or chemiluminescent moieties may be suitably utilized. After the solution of receptor conjugate has flowed through the solid phase system, a washing solution may be added to remove unbound receptor conjugate. Thereafter, the receptor conjugate complexed with the ligand of interest is detected. If an enzyme has been selected as the label component, the bound receptor conjugate is detected by the addition of an appropriate enzyme substrate to the solid phase system. Upon reaction with the substrate, the enzyme will generate, if properly selected, a color change on the solid phase system which may be detected by visual or instrumental means.

It will be recognized by those skilled in the art that assays for a broad range of analytes may be performed in accordance with the present invention. The list of potential analytes of interest is too lengthy for incorporation herein. However, antigens such as prostatic acid phosphatase, prostate-specific antigen, alphafetoprotein, carcinoembryonic antigen, leutenizing hormone, creatine kinase isoenzimes and other antigens in serum, plasma, urine or other biological fluids may be detected in an immunoassay. Additionally, the present invention is useful for the assay of viruses, bacteria, parasites or fungi, or antigens or antibodies associated therewith, including, for example, Rubella virus, Rota virus, adeno virus, respiratory syncitial virus, HTLV, hepatitis virus, hepatitis/A, hepatitis/B, hepatitis nonA nonB, influenza virus, cytomegalovirus and herpes virus, as well as group A and group B streptococcus, *Neisseria gonorrhea, Trichomonas vaginalis, Candida albicans, Chlamydia trachomatis* and *Hemophilus influenza.*

Further, it will be appreciated by those skilled in the art having the benefit of this disclosure that the present invention is applicable to assays involving nucleic acid probe technology. Specifically, a nucleic acid sequence complementary to a portion of the nucleic acid sequence of a ligand of interest may be bound to microspheres which are thereafter entrapped in a porous matrix. Such a solid phase system may be incorporated in an apparatus as previously described and utilized in assay processes. To perform such assay processes, a fluid sample suspected of containing the target ligand is introduced onto the solid phase and the ligand of interest is captured on the solid phase. Thereafter, a labeled nucleic acid probe having a nucleic acid sequence complementary to a different portion of the nucleic acid sequence of the target ligand is added to permit the formation of a complex of the labeled nucleic acid probe and the ligand captured on the solid phase. The detection of the labeled nucleic acid probe bound to the solid phase system provides an indication of the presence of the analyte in a given sample.

The following examples demonstrate the preparation of a solid phase system comprising microspheres entrapped within a glass fiber filter and the use of such a solid phase system to perform an immunoassay in accordance with the present invention. The examples are presented solely for purposes of illustration are not intended to limit the present invention in any way.

EXAMPLE I DETECTION OF ANTIGEN

The assay set forth in the following example is an immunoassay for the detection of human choriogonadotropin (HCG), an antigen present in elevated levels in the urine of pregnant women.

Activation of Microspheres

A monodisperse latex of polystyrene microspheres, 0.8 microns in diameter (Interfacial Dynamics Corporation, Portland, Oreg.) were selected and activated by passive absorption of a preparation of monoclonal antibody derived from hybrid cell line HCU 061 (Hybritech Incorporated, San Diego, Calif.), specific for the HCG antigen. The microsphere size was selected to be compatible with Whatman GF/F glass fiber filter (Whatman Company, Clifton, N.J.) by preliminary experimentation using fluorescent-labeled microspheres to determine retention within the filter. The monoclonal antibodies were obtained from ascites fluid and purified by $Na_2SO_4$ precipitation and DEAE ion exchange chromatography using standard methodology.

The antibody-bound microspheres were then backcoated with a 1% solution of Bovine Serum Albumin (BSA) in 50 mM phosphate (pH 8.0) to reduce non-specific binding of HCG and labeled antibody, following conventional procedures.

Entrapment of Microspheres

Figure 6:
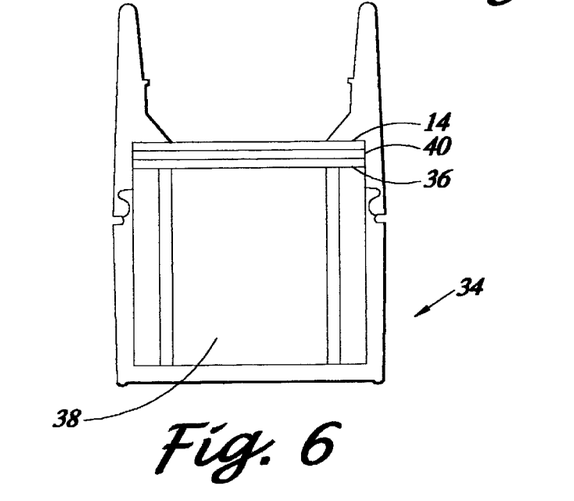
FIG. 6 is a cross section of an apparatus incorporating a solid phase system of the present invention for performance of assays in accordance with the invention.

A 10 µl quantity of the activated microspheres were resuspended in 50 mM phosphate (pH 8.0) at 0.25% w/v concentration and pipetted onto the Whatman GF/F glass fiber filter incorporated in an immunoconcentration apparatus as shown in FIG. 6. The microspheres were thereafter allowed to settle within the filter in a discrete circular zone at the center of the filter. The filter was allowed to air dry for 15 minutes.

Detection of Antigen

Approximately 250 µl of urine containing 125 mIU/ml HCG were applied to the filter. Approximately 100 µl of a preparation of a second monoclonal antibody against HCG, derived from hybrid cell line HCO 514, and labeled with the enzyme alkaline phosphatase, was then added. After a 5 minute incubation during which time the enzyme-labeled antibody conjugate was drawn through the filter, the filter was washed with 2 ml of 10 mM Trisbuffered saline (pH 8.0). Approximately 100 µl of a solution containing indoxyl phosphate, a substrate for the enzyme label was then added. After 5 minutes of incubation the filter was observed visually for a color reaction.

A dark blue color developed in the discrete zone of the filter where the HCU-061 activated microspheres were entrapped, indicating the presence of HCG antigen.

EXAMPLE II ANTIBODY DETECTION

Antibodies to Rubella virus were detected in a manner similar to that described above for detection of HCG antigen in Example I. Microspheres of 0.8 microns in diameter which had been activated with purified Rubella antigen were entrapped in a discrete zone on the Whatman GF/F glass fiber filter incorporated in an immunoconcentration apparatus as shown in FIG. 6. As a negative control, a group of non-antigen coated microspheres were entrapped in an adjacent zone on the filter.

Detection of Antibodies

A 100 µl quantity of serum predetermined to be positive for the presence of antibodies to Rubella virus was applied onto a second filter prepared as described above.

Simultaneously, a 100 µl quantity of serum predetermined to be negative for the presence of anti-bodies was added onto each filter with 2 ml of 10 mM Tris-buffered saline (pH 8.0), 100 µl of enzyme conjugated-antibodies against human IgG (Kirkegaard & Perry Laboratories, Inc., Gaithersburg, Md.) and allowed to react with the human IgG complexed with the Rubella antigen bound to the microspheres. After washing with 2 ml of 10 mM Tris-buffered saline (pH 8.0) to remove unbound conjugate, substrate for the enzyme label was added to detect the presence of any antigen-antibody complexes formed.

The positive sera resulted in a blue color in the discrete zone of the filter where microspheres bound with Rubella antigen were entrapped. (In the zone of the negative control, no color appeared.) The negative sera did not produce a color reaction.

It will be appreciated that the sensitivity of the assays of the examples may be adjusted by varying the volume and concentration of the microspheres, or incubation time, conjugate concentration, and other parameters commonly used in assay procedures.

The foregoing description has been directed to particular embodiments of the invention in accordance with the requirements of the Patent Statutes for the purposes of illustration and explanation. It will be apparent, however, to those skilled in the art that many modifications and changes will be possible without departing from the spirit and scope of the invention. It is intended that the following claims be interpreted to embrace all such modifications and changes.

What is claimed is:

1. A solid phase system for use in a ligand-receptor assay for the detection of a selected analyte in a fluid sample comprising:
   a porous matrix having a top surface onto which the fluid sample is applied, and a given thickness, said top surface having pore openings, and
   microparticles bound with a receptor capable of binding a target ligand, said microparticles being of a size less than the size of at least some of said openings in said top surface, wherein said microparticles are retained in said matrix in
   a) an area of said top surface onto which the fluid sample is applied, with
   b) at least some of said microparticles being retained within the thickness of said matrix.

2. The solid phase system according to claim 1 wherein said matrix is a membrane or filter.

3. The solid phase system according to claim 2 wherein said microparticles are selected to have a size within a range of from about 0.1 micron to about 50 microns in diameter.

4. The solid phase system according to claim 2 wherein said microparticles are selected to have a size within a range of from about 0.1 micron to about 2.0 microns in diameter.

5. The solid phase system according to claim 2 wherein said membrane or filter is of a material selected from the group consisting of glass fibers, nylon and ceramic materials.

6. The solid phase system according to claim 1 wherein said microparticles are comprised of a polymeric material capable of being bound with said receptor.

7. The solid phase system according to claim 6 wherein said microparticles are comprised of a material selected from the group consisting of latex, polyethylene, polypropylene, polystyrene and copolymers thereof.

8. The solid phase system according to claim 7 wherein said microparticles comprise latex.

9. The solid phase system according to claim 1 wherein said ligand-receptor assay is an immunoassay.

10. The solid phase system according to claim 9 wherein said receptor bound with said microparticles is an antibody or antigen capable of binding said target ligand.

11. The solid phase system according to claim 10 wherein said antibody is a monoclonal antibody.

12. An apparatus for use in a ligand-receptor assay for the detection of at least one selected analyte in a fluid sample comprising:
   a) a first porous member comprising a solid phase system according to claim 1; and
   b) a means, operatively associated with said first porous member, for facilitating the flow of said fluid sample and liquid reagents used in said assay through said first porous member.

13. The apparatus according to claim 12 wherein said receptor and target ligand are nucleic acids capable of hybridizing to one another.

14. A ligand-receptor assay process for the detection of at least one target ligand in a fluid sample comprising:
   a) introducing said fluid sample suspected of containing a target ligand onto the first porous member of the apparatus according to claim 12, said porous member comprising microparticles to which are bound a receptor capable of binding said target ligand;
   b) adding a solution of receptor conjugate capable of binding with said target ligand, said receptor conjugate being labeled to permit detection, in order to form a complex of said receptor conjugate with said target ligand; and
   c) detecting said target ligand by detecting said receptor conjugate, if any, bound to said porous member.

15. The process according to claim 14 wherein said ligand-receptor assay is an immunoassay.

16. The process according to claim 14 wherein said receptor is an allergen, said ligand is an IgE antibody specific for said allergen and said receptor conjugate is a labeled anti-IgE antibody.

17. The process according to claim 14 wherein said target ligand is a virus or an antigen whose presence indicates the presence of said virus or an antibody produced by an immune response to said virus.

18. A process according to claim 17 wherein said ligand is selected from the group consisting of Rubella virus, Rota virus, adeno virus, respiratory syncitial virus, HTLV, hepatitis virus, influenza virus, cytomegalovirus and herpes virus.

19. The process according to claim 18 wherein said ligand is selected from the group consisting of hepatitis A, hepatitis B, and hepatitis non-A, non-B.

20. The process according to claim 14 wherein said target ligand is a bacterium, fungus or parasite or an antigen or antibody whose presence indicates the presence of said bacterium, fungus or parasite.

21. A process according to claim 20 wherein said analyte is selected from the group consisting of group A and B streptococcus, *Neisseria gonorrhea, Trichomonas vaginalis, Candida albicans, Chlamydia trachomatis* and *Hemophilus influenza*.

22. The process according to claim 14 wherein said analyte is a physiological marker substance selected from the group consisting of human choriogonadotropin, prostatic acid phosphatase, prostrate-specific antigen, alpha-fetoprotein, carcino-embryonic antigen, leutinizing hormone and creatine kinase isoenzyme.

23. The process according to claim 14 wherein said sample is serum, plasma, urine or other biological fluid.

24. The process according to claim 14 wherein said receptor conjugate is labeled with an enzyme and said detecting step includes addition of a substrate specific for said enzyme to said first porous member to generate a color change upon reaction with said enzyme which is determined by visual or instrumental means.

25. The process according to claim 14 wherein said receptor is a monoclonal antibody and said receptor conjugate is a labeled monoclonal antibody, said receptor and said receptor conjugate being selected to bind at non-interfering epitopes of said ligand.

26. The process according to claim 14 wherein said receptor is a nucleic acid sequence complementary to a portion of the nucleic acid sequence of said target ligand and said receptor conjugate is a labeled nucleic acid probe complementary to another portion of the nucleic acid sequence of said target ligand.

27. An apparatus for use in a ligand-receptor assay for the detection of at least one target ligand in a fluid sample comprising:
   a) a first porous member comprising a solid phase system according to claim 1; and
   b) a second absorbent member associated with said first member so as to permit the flow of said fluid sample and liquid reagents used in said assay through said first member and into said second member, said second member having a surface over which said first member is placed and having capillaries therethrough which are in communication with the pores of said first member so as to draw fluid which has permeated said first member into the capillaries of said second member.

28. The apparatus according to claim 27 wherein said apparatus further comprises a third porous member which separates said first porous member from said second absorbent member and permits the flow of a fluid sample and liquid reagents through said first porous member and into said second absorbent member.

29. The apparatus according to claim 28 wherein said apparatus further comprises a fourth porous member which separates said first porous member and said third porous member and maintains the flow of a fluid sample and liquid reagents through said first porous member and into said second absorbent member.

30. The solid phase system according to claim 1 wherein said assay is a nucleic acid probe assay and wherein said receptor comprises a nucleic acid sequence complementary to a portion of the nucleic acid sequence of said target ligand.

31. A solid phase system for use in a multiple ligand-receptor assay for the simultaneous detection of at least two target ligand in a fluid sample comprising:

a porous matrix having a top surface onto which the fluid sample is applied, and a given thickness, said top surface having pore openings, and distinct groups of substantially spherical microparticles, said microparticles being of a size less than the size of at least some of said pore openings in said top surface, wherein said distinct groups of microparticles are retained in said matrix
   a) in discrete areas that are within and are smaller than the area of said top surface onto which the fluid sample is applied, with
   b) at least some of said microparticles being retained within the thickness of said matrix; and wherein
   c) each of said distinct groups of microparticles is bound with a receptor capable of binding a different target ligand.

32. The solid phase system according to claim 31 wherein said matrix is a membrane or filter.

33. The solid phase system according to claim 32 wherein said membrane or filter is of a material selected from the group consisting of glass fibers, nylon and ceramic materials.

34. The solid phase system according to claim 31 wherein said microparticles are comprised of a polymeric material capable of being bound with said receptor.

35. The solid phase system according to claim 34 wherein said microparticles are comprised of a material selected from the group consisting of latex, polyethylene, polypropylene, polystyrene and copolymers thereof.

36. The solid phase system according to claim 35 wherein said microparticles comprise latex.

37. The solid phase system according to claim 31 wherein said ligand-receptor assay is an immunoassay.

38. The solid phase system according to claim 37 wherein said receptor bound with at least one group of microparticles is an antibody or antigen capable of binding said target ligand.

39. The solid phase system according to claim 38 wherein said antibody is a monoclonal antibody.

40. The solid phase system according to claim 39 wherein at least one of said different groups of microparticles comprises at least two different subpopulations of microparticles to which are bound at least two different monoclonal antibodies selected to bind non-interfering epitopes of said target ligand.

41. An apparatus for use in a ligand-receptor assay for the detection of at least one selected analyte in a fluid sample comprising:

a) a first porous member comprising a solid phase system according to claim 31; and
b) a means, operatively associated with said first porous member, for facilitating the flow of said fluid sample and liquid reagents used in said assay through said first porous member.

42. The apparatus according to claim 41 wherein said receptor and target ligand are nucleic acids capable of hybridizing to one another.

43. A ligand-receptor assay process for the detection of at least one target ligand in a fluid sample comprising:

a) introducing said fluid sample suspected of containing a target ligand onto the first porous member of the apparatus according to claim 41, said porous member comprising microparticles to which are bound a receptor capable of binding said target ligand;
b) adding a solution of receptor conjugate capable of binding with said target ligand, said receptor conjugate being labeled to permit detection, in order to form a complex of said receptor conjugate with said target ligand; and
c) detecting said target ligand by detecting said receptor conjugate, if any, bound to said porous member.

44. The process according to claim 43 wherein said ligand-receptor assay is an immunoassay.

45. The process according to claim 43 wherein said receptor is a nucleic acid sequence complementary to a portion of the nucleic acid sequence of said target ligand and said receptor conjugate is a labeled nucleic acid probe complementary to another portion of the nucleic acid sequence of said target ligand.

46. An apparatus for use in a ligand-receptor assay for the detection of at least one target ligand in a fluid sample comprising:

a) a first porous member comprising a solid phase system according to claim 31; and
b) a second absorbent member associated with said first member so as to permit the flow of said fluid sample and liquid reagents used in said assay through said first member and into said second member, said second member having a surface over which said first member is placed and having capillaries therethrough which are in communication with the pores of said first member so as to draw fluid which has permeated said first member into the capillaries of said second member.

47. The apparatus according to claim 46 wherein said apparatus further comprises a third porous member which separates said first porous member from said second absorbent member and permits the flow of a fluid sample and liquid reagents through said first porous member and into said second absorbent member.

48. The apparatus according to claim 47 wherein said apparatus further comprises a fourth porous member which separates said first porous member and said third porous member and maintains the flow of a fluid sample and liquid reagents through said first porous member and into said second absorbent member.

49. The solid phase system according to claim 31 wherein said assay is a nucleic acid probe assay and wherein said receptor comprises a nucleic acid sequence complementary to a portion of the nucleic acid sequence of said target ligand.

50. A solid phase system for use in a ligand-receptor assay for the detection of at least one target ligand in a fluid sample comprising:

a porous matrix having a top surface onto which the fluid sample is applied, and a given thickness, said top surface having pore openings, and distinct groups of substantially spherical microparticles, said microparticles being of a size less than the size of at least some of said pore openings in said top surface, wherein said distinct groups of microparticles are retained in said matrix
  a) in an area that is within and is smaller than the area of said top surface to which the fluid sample is applied, with
  b) at least some of said microparticles being retained within the thickness of said matrix; and wherein
  c) at least one group of microparticles is bound with a receptor capable of binding a target ligand; and
  d) at least one group of microparticles is bound with a said target ligand or other receptor capable of binding the receptor of step c) as a positive control for the detection of said target ligand.

51. The solid phase system according to claim 50 wherein said matrix is a membrane or filter.

52. The solid phase system according to claim 51 wherein said membrane or filter is of a material selected from the group consisting of glass fibers, nylon and ceramic materials.

53. The solid phase system according to claim 50 wherein said microparticles are comprised of a polymeric material capable of being bound with said receptor.

54. The solid phase system according to claim 53 wherein said microparticles are comprised of a material selected from the group consisting of latex, polyethylene, polypropylene, polystyrene and copolymers thereof.

55. The solid phase system according to claim 54 wherein said microparticles comprise latex.

56. The solid phase system according to claim 50 wherein said ligand-receptor assay is an immunoassay.

57. The solid phase system according to claim 56 wherein said receptor bound with at least one group of microparticles is an antibody or antigen capable of binding said target ligand.

58. The solid phase system according to claim 57 wherein said antibody is a monoclonal antibody.

59. An apparatus for use in a ligand-receptor assay for the detection of at least one selected analyte in a fluid sample comprising:
  a) a first porous member comprising a solid phase system according to claim 50; and
  b) a means, operatively associated with said first porous member, for facilitating the flow of said fluid sample and liquid reagents used in said assay through said first porous member.

60. A ligand-receptor assay process for the detection of at least one target ligand in a fluid sample comprising:
  a) introducing said fluid sample suspected of containing a target ligand onto the first porous member of the apparatus according to claim 59, said porous member comprising microparticles to which are bound a receptor capable of binding said target ligand;
  b) adding a solution of receptor conjugate capable of binding with said target ligand, said receptor conjugate being labeled to permit detection, in order to form a complex of said receptor conjugate with said target ligand; and
  c) detecting said target ligand by detecting said receptor conjugate, if any, bound to said porous member.

61. The process according to claim 60 wherein said ligand-receptor assay is an immunoassay.

62. The process according to claim 60 wherein said receptor is a nucleic acid sequence complementary to a portion of the nucleic acid sequence of said target ligand and said receptor conjugate is a labeled nucleic acid probe complementary to another portion of the nucleic acid sequence of said target ligand.

63. The apparatus according to claim 59 wherein said receptor and target ligand are nucleic acids capable of hybridizing to one another.

64. An apparatus for use in a ligand-receptor assay for the detection of at least one target ligand in a fluid sample comprising:
  a) a first porous member comprising a solid phase system according to claim 50; and
  b) a second absorbent member associated with said first member so as to permit the flow of said fluid sample and liquid reagents used in said assay through said first member and into said second member, said second member having a surface over which said first member is placed and having capillaries therethrough which are in communication with the pores of said first member so as to draw fluid which has permeated said first member into the capillaries of said second member.

65. The apparatus according to claim 64 wherein said apparatus further comprises a third porous member which separates said first porous member from said second absorbent member and permits the flow of a fluid sample and liquid reagents through said first porous member and into said second absorbent member.

66. The apparatus according to claim 65 wherein said apparatus further comprises a fourth porous member which separates said first porous member and said third porous member and maintains the flow of a fluid sample and liquid reagents through said first porous member and into said second absorbent member.

67. The solid phase system according to claim 50 wherein said assay is a nucleic acid probe assay and wherein said receptor comprises a nucleic acid sequence complementary to a protion of the nucleic acid sequence of said target ligand.

68. A solid phase system for use in a ligand-receptor assay for the detection of at least one target ligand in a fluid sample comprising:
  a porous matrix having a top surface onto which the fluid sample is applied, and a given thickness, said top surface having pore openings, and
  distinct groups of substantially spherical microparticles, said microparticles being of a size less than the size of at least some of said openings in said top surface, wherein said distinct groups of microparticles are retained in said matrix
    a) in an area that is within and is smaller than the area of said top surface to which the fluid sample is applied, with
    b) at least some of said microparticles being retained within the thickness of said matrix; and wherein
    c) at least one group of microparticles is bound with a receptor capable of binding a target ligand; and
    d) at least one group of microparticles is bound with a substance incapable of binding said target ligand, or is without a bound component, as a negative control for the detection of said target ligand.

69. The solid phase system according to claim 68 wherein said matrix is a membrane or filter.

70. The solid phase system according to claim 69 wherein said membrane or filter is of a material selected from the group consisting of glass fibers, nylon and ceramic materials.

71. The solid phase system according to claim 68 wherein said microparticles are comprised of a polymeric material capable of being bound with said receptor.

72. The solid phase system according to claim 71 wherein said microparticles are comprised of a material selected from the group consisting of latex, polyethylene, polypropylene, or polystyrene and copolymers thereof.

73. The solid phase system according to claim 72 wherein said microparticles comprise latex.

74. The solid phase system according to claim 68 wherein said ligand-receptor assay is an immunoassay.

75. The solid phase system according to claim 74 wherein said receptor bound with at least one group of microparticles is an antibody or antigen capable of binding said target ligand.

76. The solid phase system according to claim 75 wherein said antibody is a monoclonal antibody.

77. An apparatus for use in a ligand-receptor assay for the detection of at least one selected analyte in a fluid sample comprising:
   a) a first porous member comprising a solid phase system according to claim 68; and
   b) a means, operatively associated with said first porous member, for facilitating the flow of said fluid sample and liquid reagents used in said assay through said first porous member.

78. A ligand-receptor assay process for the detection of at least one target ligand in a fluid sample comprising:
   a) introducing said fluid sample suspected of containing a target ligand onto the first porous member of the apparatus according to claim 77, said porous member comprising microparticles to which are bound a receptor capable of binding said target ligand;
   b) adding a solution of receptor conjugate capable of binding with said target ligand, said receptor conjugate being labeled to permit detection, in order to form a complex of said receptor conjugate with said target ligand; and
   c) detecting said target ligand by detecting said receptor conjugate, if any, bound to said porous member.

79. The process according to claim 78 wherein said ligand-receptor assay is an immunoassay.

80. The process according to claim 78 wherein said receptor is a nucleic acid sequence complementary to a portion of the nucleic acid sequence of said target ligand and said receptor conjugate is a labeled nucleic acid probe complementary to another portion of the nucleic acid sequence of said target ligand.

81. The apparatus according to claim 77 wherein said receptor and target ligand are nucleic acids capable of hybridizing to one another.

82. An apparatus for use in a ligand-receptor assay for the detection of at least one target ligand in a fluid sample comprising:
   a) a first porous member comprising a solid phase system according to claim 68; and
   b) a second absorbent member associated with said first member so as to permit the flow of said fluid sample and liquid reagents used in said assay through said first member and into said second member, said second member having a surface over which said first member is placed and having capillaries therethrough which are in communication with the pores of said first member so as to draw fluid which has permeated said first member into the capillaries of said second member.

83. The apparatus according to claim 82 wherein said apparatus further comprises a third porous member which separates said first porous member from said second absorbent member and permits the flow of a fluid sample and liquid reagents through said first porous member and into said second absorbent member.

84. The apparatus according to claim 83 wherein said apparatus further comprises a fourth porous member which separates said first porous member and said third porous member and maintains the flow of a fluid sample and liquid reagents through said first porous member and into said second absorbent member.

85. The solid phase system according to claim 68 wherein said assay is a nucleic acid probe assay and wherein said receptor comprises a nucleic acid sequence complementary to a portion of the nucleic acid sequence of said target ligand.

86. A solid phase system for use in a ligand-receptor assay for the detection of at least one target ligand in a fluid sample comprising:
   a porous matrix having a top surface onto which the fluid sample is applied, and a given thickness, said top surface having pore openings, and
   distinct groups of substantially spherical microparticles, said microparticles being of a size less than the size of at least some of said pore openings in said top surface, wherein said distinct groups of microparticles are retained in said matrix
   a) in an area that is within and is smaller than the area of said top surface to which the fluid sample is applied, with
   b) at least some of said microparticles being retained within the thickness of said matrix; and wherein
   c) at least one group of microparticles is bound with a receptor capable of binding a target ligand; and
   d) at least one group of microparticles is bound with a reference receptor for qualitative detection of said target ligand in said sample.

87. An apparatus for use in a ligand-receptor assay for the detection of at least one target ligand in a fluid sample comprising:
   a) a first porous member comprising a solid phase system according to claim 86; and
   b) a second absorbent member associated with said first member so as to permit the flow of said fluid sample and liquid reagents used in said assay through said first member and into said second member, said second member having a surface over which said first member is placed and having capillaries therethrough which are in communication with the pores of said first member so as to draw fluid which has permeated said first member into the capillaries of said second member.

88. The apparatus according to claim 87 wherein said apparatus further comprises a third porous member which separates said first porous member from said second absorbent member and permits the flow of a fluid sample and liquid reagents through said first porous member and into said second absorbent member.

89. The apparatus according to claim 88 wherein said apparatus further comprises a fourth porous member which separates said first porous member and said third porous member and maintains the flow of a fluid sample and liquid reagents through said first porous member and into said second absorbent member.

90. A ligand-receptor assay process for the detection of at least one target ligand in a fluid sample comprising:
   a) introducing said fluid sample suspected of containing a target ligand onto the first porous member of the apparatus according to claim 87 said porous member comprising microparticles to which are bound a receptor capable of binding said target ligand;

b) adding a solution of receptor conjugate capable of binding with said target ligand, said receptor conjugate being labeled to permit detection, in order to form a complex of said receptor conjugate with said target ligand; and c) detecting said receptor conjugate, if any, bound to said porous member.

91. A solid phase system for use in a ligand-receptor assay for the detection or determination of at least one target ligand in a fluid sample comprising:

a porous matrix having a top surface onto which the fluid sample is applied, and a given thickness, said top surface having pore openings, and distinct groups of substantially spherical microparticles, said microparticles being of a size less than the size of at least some of said openings in said top surface, wherein said distinct groups of microparticles are retained in said matrix a) in an area that is within and is smaller than the area of said top surface to which the fluid sample is applied, with b) at least some of said microparticles being retained within the thickness of said matrix; and wherein c) at least one group of microparticles is bound with a receptor capable of binding a target ligand; and d) at least two groups of microparticles are bound with a reference receptor for qualitative or quantitative determination of said target ligand in said sample.

92. An apparatus for use in a ligand-receptor assay for the detection of at least one target ligand in a fluid sample comprising:

a) a first porous member comprising a solid phase system according to claim 91; and b) a second absorbent member associated with said first member so as to permit the flow of said fluid sample and liquid reagents used in said assay through said first member and into said second member, said second member having a surface over which said first member is placed and having capillaries therethrough which are in communication with the pores of said first member so as to draw fluid which has permeated said first member into the capillaries of said second member.

93. The apparatus according to claim 92 wherein said apparatus further comprises a third porous member which separates said first porous member from said second absorbent member and permits the flow of a fluid sample and liquid reagents through said first porous member and into said second absorbent member.

94. The apparatus according to claim 93 wherein said apparatus further comprises a fourth porous member which separates said first porous member and said third porous member and maintains the flow of a fluid sample and liquid reagents through said first porous member and into said second absorbent member.

95. A ligand-receptor assay process for the detection of at least one target ligand in a fluid sample comprising:

a) introducing said fluid sample suspected of containing a target ligand onto the first porous member of the apparatus according to claim 92, said porous member comprising microparticles to which are bound a receptor capable of binding said target ligand;

b) adding a solution of receptor conjugate capable of binding with said target ligand, said receptor conjugate being labeled to permit detection, in order to form a complex of said receptor conjugate with said target ligand; and c) detecting said receptor conjugate, if any, bound to said porous member.

96. A solid phase system for use in a ligand-receptor assay for the detection of a target ligand in a fluid sample comprising:

a porous matrix having a top surface onto which the fluid sample is applied, and a given thickness, said top surface having pore openings, and substantially spherical microparticles bound with a receptor capable of binding a target ligand, said microparticles being of a size less than the size of at least some of said pore openings in said top surface, wherein said microparticles are retained in said matrix a) in an area that is within and is smaller than the area of said top surface onto which the fluid sample is applied, with b) at least some of said microparticles being retained within the thickness of said matrix.

97. The solid phase system according to claim 96 wherein said matrix is a membrane or filter.

98. The solid phase system according to claim 97 wherein said microparticles are selected to have a size within a range of from about 0.1 micron to about 50 microns in diameter.

99. The solid phase system according to claim 97 wherein said microparticles are selected to have a size within a range of from about 0.1 micron to about 2.0 microns in diameter.

100. The solid phase system according to claim 96 wherein said membrane or filter is of a material selected from the group consisting of glass fibers, nylon and ceramic materials.

101. The solid phase system according to claim 96 wherein said microparticles are comprised of a polymeric material capable of being bound with said receptor.

102. The solid phase system according to claim 101 wherein said microparticles are comprised of a material selected from the group consisting of latex, polyethylene, polypropylene, polystyrene and copolymers thereof.

103. The solid phase system according to claim 96 wherein said ligand-receptor assay is an immunoassay.

104. The solid phase system according to claim 103 wherein said receptor bound with said microparticles is an antibody or antigen capable of binding said target ligand.

105. The solid phase system according to claim 104 wherein said antibody is a monoclonal antibody.

106. An apparatus for use in a ligand-receptor assay for the detection of at least one target ligand in a fluid sample comprising:

a) a first porous member comprising a solid phase system according to claim 96; and b) a second absorbent member associated with said first member so as to permit the flow of said fluid sample and liquid reagents used in said assay through said first member and into said second member, said second member having a surface over which said first member is placed and having capillaries therethrough which are in communication with the pores of said first member so as to draw fluid which has permeated said first member into the capillaries of said second member.

107. The apparatus according to claim 106 wherein said apparatus further comprises a third porous member which separates said first porous member from said second absorbent member and permits the flow of a fluid sample and liquid reagents through said first porous member and into said second absorbent member.

108. The apparatus according to claim 107 wherein said apparatus further comprises a fourth porous member which separates said first porous member and said third porous member and maintains the flow of a fluid sample and liquid reagents through said first porous member and into said second absorbent member.

109. A ligand-receptor assay process for the detection of at least one target ligand in a fluid sample comprising:
   a) introducing said fluid sample suspected of containing a target ligand onto the first porous member of the apparatus according to claim 106, said porous member comprising microparticles to which are bound a receptor capable of binding said target ligand;
   b) adding a solution of receptor conjugate capable of binding with said target ligand, said receptor conjugate being labeled to permit detection, in order to form a complex of said receptor conjugate with said target ligand; and
   c) detecting said receptor conjugate, if any, bound to said porous member.

110. A solid phase system for use in a ligand-receptor assay for the detection of at least one target ligand in a fluid sample comprising:
   a porous matrix having a top surface onto which the fluid sample is applied, and a given thickness, said top surface having pore openings, and
   distinct groups of substantially spherical microparticles, said microparticles being of a size less than the size of at least some of said pore openings in said top surface, wherein said distinct groups of microparticles are retained in said matrix
      a) in an area that is within and is smaller than the area of said top surface to which the fluid sample is applied, with
      b) at least some of said microparticles being retained within the thickness of said matrix; and wherein
      c) at least one group of microparticles is bound with a receptor capable of binding a target ligand; and
      d) at least one group of microparticles is bound with a said target ligand or other receptor capable of binding the receptor of step c) as a positive control for the detection of said target ligand; and
      (e) at least one group of microparticles is bound with a substance incapable of binding said target ligand, or is without a bound component, as a negative control for the detection of said target ligand.

111. The solid phase system according to claim 110 wherein said matrix is a membrane or filter.

112. The solid phase system according to claim 110 wherein said membrane or filter is of a material selected from the group consisting of glass fibers, nylon and ceramic materials.

113. The solid phase system according to claim 110 wherein said microparticles are selected to have a size within a range of from about 0.1 micron to about 50 microns in diameter.

114. The solid phase system according to claim 110 wherein said microparticles are selected to have a size within a range of from about 0.1 micron to about 2.0 microns in diameter.

115. The solid phase system according to claim 110 wherein said membrane or filter is of a material selected from the group consisting of glass fibers, nylon and ceramic materials.

116. The solid phase system according to claim 115 wherein said microparticles are comprised of a polymeric material capable of being bound with said receptor.

117. The solid phase system according to claim 110 wherein said microparticles are comprised of a material selected from the group consisting of latex, polyethylene, polypropylene, polystyrene and copolymers thereof.

118. The solid phase system according to claim 117 wherein said ligand-receptor assay is an immunoassay.

119. The solid phase system according to claim 118 wherein said receptor bound with said microparticles is an antibody or antigen capable of binding said target ligand.

120. The solid phase system according to claim 119 wherein said antibody is a monoclonal antibody.

121. An apparatus for use in a ligand-receptor assay for the detection of at least one target ligand in a fluid sample comprising:
   a) a first porous member comprising a solid phase system according to claim 110; and
   b) a second absorbent member associated with said first member so as to permit the flow of said fluid sample and liquid reagents used in said assay through said first member and into said second member, said second member having a surface over which said first member is placed and having capillaries therethrough which are in communication with the pores of said first member so as to draw fluid which has permeated said first member into the capillaries of said second member.

122. The apparatus according to claim 121 wherein said apparatus further comprises a third porous member which separates said first porous member from said second absorbent member and permits the flow of a fluid sample and liquid reagents through said first porous member and into said second absorbent member.

123. The apparatus according to claim 122 wherein said apparatus further comprises a fourth porous member which separates said first porous member and said third porous member and maintains the flow of a fluid sample and liquid reagents through said first porous member and into said second absorbent member.

124. A ligand-receptor assay process for the detection of at least one target ligand in a fluid sample comprising:
   a) introducing said fluid sample suspected of containing a target ligand onto the first porous member of the apparatus according to claim 121, said porous member comprising microparticles to which are bound a receptor capable of binding said target ligand;
   b) adding a solution of receptor conjugate capable of binding with said target ligand, said receptor conjugate being labeled to permit detection, in order to form a complex of said receptor conjugate with said target ligand; and
   c) detecting said receptor conjugate, if any, bound to said porous member.

125. The process according to claim 90, 95, 109 or 124 wherein said ligand-receptor assay is an immunoassay.

* * * * *